United States Patent
Shirazi et al.

(10) Patent No.: US 9,220,741 B2
(45) Date of Patent: Dec. 29, 2015

(54) WEIGHT LOSS FORMULATION

(75) Inventors: Shawn Shirazi, Oakville (CA); James Akrong, Oakville (CA); Phil Apong, Oakville (CA); Raza Bashir, Oakville (CA); Craig Wissent, Oakville (CA)

(73) Assignee: Northern Innovations and Formulations Corp., Oakville, Ontario, CA (US)

( * ) Notice: Subject to any disclaimer, the term of this patent is extended or adjusted under 35 U.S.C. 154(b) by 1028 days.

(21) Appl. No.: 13/221,141

(22) Filed: Aug. 30, 2011

(65) Prior Publication Data

US 2012/0052137 A1    Mar. 1, 2012

Related U.S. Application Data

(60) Provisional application No. 61/378,098, filed on Aug. 30, 2010.

(51) Int. Cl.

| | | |
|---|---|---|
| *A61K 36/81* | (2006.01) | |
| *A61K 36/752* | (2006.01) | |
| *A61K 36/45* | (2006.01) | |
| *A61K 36/48* | (2006.01) | |
| *A61K 36/54* | (2006.01) | |
| *A61K 36/82* | (2006.01) | |
| *A61K 36/886* | (2006.01) | |

(52) U.S. Cl.
CPC ............... *A61K 36/752* (2013.01); *A61K 36/45* (2013.01); *A61K 36/48* (2013.01); *A61K 36/54* (2013.01); *A61K 36/81* (2013.01); *A61K 36/82* (2013.01); *A61K 36/886* (2013.01)

(58) Field of Classification Search
None
See application file for complete search history.

(56) References Cited

U.S. PATENT DOCUMENTS

2009/0214680 A1*   8/2009   Giuliano et al. .............. 424/728

OTHER PUBLICATIONS

Visentainer et al., Vitamin C in Barbados cherry Malpighia glabra L. pulp submitted to processing and to different forms of storage, 1998, Arch Latinoam Nutr, 48: 256-9.*
EFSA: Scientific Opinion on the Safety of 'Conjugated Linoleic Acid (CLA)-Rich Oil' (Tonalin® TG 80) As a Novel Food Ingredient; EFSA Journal 2010; 8(5):1000 pp. 1-43).*
Said, O., et al., "A Double Blinded-Randomized Clinical Study with 'Weighlevel,' a Combination of Four Medicinal Plants Used in Traditional Greco-Arab and Islamic Medicine," The Open Complementary Medicine Journal, 2010, 2, pp. 1-6.
Said, O., et al., "Weight Loss in Animals and Humans Treated with 'Weighlevel', a Combination of Four Medicinal Plants Used in Traditional Greco-Arab and Islamic Medicine," eCAM Advance Access published Oct. 24, 2008, pp. 1-7.
Said, O., et al.,"Weight Loss in Animals and Humans Treated with 'Weighlevel,' a Combination of Four Medicinal Plants Used in Traditional Greco-Arab and Islamic Medicine," Evidence Based Complementary and Alternative Medicine, vol. 2011, Article ID 874538, pp. 1-6.
Sprunk-Jansen LLC Press Release on WEIGHLEVEL study, Feb. 2010.

* cited by examiner

*Primary Examiner* — Terry A McKelvey
*Assistant Examiner* — Catheryne Chen
(74) *Attorney, Agent, or Firm* — David M. Quinlan, P.C.

(57) ABSTRACT

A method of enhancing weight loss involves administering to an overweight human a weight loss product that includes a mixture of *Alchemilla vulgaris, Olea europaea, Cuminum cyminum*, and *Mentha longiflora* (in the weight proportion 12:10:5:4), to which is added at least one herbal ingredient such as *Malpighia glabra*. As additional ingredients at least one of Conjugated linoleic acid and caffeine can be provided, with the caffeine in the form of caffeine anhydrous, *Coffea Arabica, Coffea canephora, Camellia sinensis, Ilex paraguariensis, Guarana, Theobroma cacao*, and kola nut. In one preferred embodiment the method involves administering, optionally in tablet form, a composition consisting essentially of the mixture of *Alchemilla vulgaris, Olea europaea, Cuminum cyminum*, and *Mentha longiflora*; caffeine anhydrous; Vitamin C; *Lyceum barbarum; Malpighia glabra*; Blueberry; *Punica granatum*; Bilberry; and one or more excipients. Other ingredients may be used as well in accordance with specific disclosed formulations.

5 Claims, No Drawings

WEIGHT LOSS FORMULATION

CROSS-REFERENCE TO RELATED APPLICATION

This application claims the benefit of U.S. provisional application No. 61/376,098, filed Aug. 30, 2010, which application is incorporated herein by reference.

BACKGROUND OF THE INVENTION

1. Field of the Invention

The present invention relates to a weight loss formulation, and more particularly, to a formulation comprising a known combination of herbal extracts to which is added further ingredients to enhance weight loss.

2. Description of Related Art

A product called Weighlevel™ marketed by Sprunk-Jansen A/S contains a mixture of the extracts of four plants that have been used in traditional folk medicine as a weight loss product. The four plants are Lady's Mantle (*Alchemilla vulgaris* L.), olive leaves (*Olea europaea* L.), cumin seed (*Cuminum cyminum* L.), and wild mint (Mentha longiflora L.). Reported studies have demonstrated the efficacy for weight loss of a daily regimen of three 310 mg tablets taken with meals, each tablet containing the following amounts of these plant extracts:

*Alchemilla vulgaris*—60 mg
*Olea europaea*—50 mg
*Cuminum cyminum*—25 mg
*Mentha longiflora.*—20 mg Said, O., et al., "Weight Loss in Animals and Humans Treated with 'Weighlevel,' a Combination of Four Medicinal Plants Used in Traditional Arabic and Islamic Medicine," *Evid Based Complement Alternate Med*, Vol. 5, pgs. 421-28 (2008) (available at http://ecam.oxfordjournals.org); Said, O., et al., "A Double Blinded-Randomized Clinical Study with 'Weighlevel,' a Combination of Four Medicinal Plants Used in Traditional Arabic and Islamic Medicine," *The Open Complementary Medicine Jour.*, Vol. 2, pgs. 1-6 (2010). (The formulations in both studies also contained 7 mg of Vitamin C and 148 mg of tricalcium phosphate).

However, there appear to be no reports of enhancing the weight loss effects of the tested Weighlevel™ herbal formulation by incorporating other ingredients in combination with extracts of *Alchemilla vulgaris, Olea europaea, Cuminum cyminum,* and *Mentha longiflora.*

SUMMARY OF THE INVENTION

It is an object of the present invention to provide various formulations of the above combination of *Alchemilla vulgaris, Olea europaea, Cuminum cyminum,* and *Mentha longiflora,* with one or more additional ingredients to enhance weight loss.

It is a further object of the invention to provide methods of administering such formulations to enhance weight loss in individuals using them.

DETAILED DESCRIPTION OF PREFERRED EMBODIMENTS

The present invention includes numerous specific formulations that comprise *Alchemilla vulgaris, Olea europaea, Cuminum cyminum,* and *Mentha longiflora,* to which additional ingredients have been added to increase the weight loss efficacy of previously known products such as Weighlevel™.

It is believed that the use of *Alchemilla vulgaris, Olea europaea, Cuminum cyminum,* and *Mentha longiflora,* particularly in combination with other ingredients such as those used in formulations according to the present invention, may further enhance weight loss in overweight but otherwise healthy individuals. That is, the studies reported in the Said et al. papers mentioned above included a large proportion of subjects on medications for ischemic heart disease, diabetes mellitus, and/or hypertension. Said et al. 2008 at page 7; Said et al. 2010 at page 3. It is possible that such medications interfere with the efficacy of such formulations in maximizing weight loss.

In addition, there is evidence that a formulation including *Alchemilla vulgaris, Olea europaea, Cuminum cyminum,* and *Mentha longiflora* in combination with other ingredients according to the present invention will cause subjects to lose more weight over the same period than the Weighlevel™ product reported in the Said et al. papers. It is also believed that weight loss is even further enhanced in female subjects.

Formulations according to embodiments of the invention comprise a mixture of *Alchemlla vulgaris, Olea europaea, Cuminum cyminum,* and *Mentha longiflora,* to which additional ingredients have been added to increase weight loss efficacy. The additional ingredients may include, but are not limited to, Gamma-oryzanol, Caffeine, Cirsimarin, Fucoxanthin, Guggulsterones, Evodiamine, Forskolin, Sclareolide, Chromium, Hydroxycitric acid, Pinolenic acid, Conjugated linoleic acid, Potato protein, Raspberry ketone, Capsaicin, Synephrine, Dehydroepiandrosterone, Phenylethylamine, Orlistat, Glucomannan, or Vitamin C, or sources thereof, as well as herbal ingredients such as Guarana, *Yerba Mate,* Damiana, Green tea, Green coffee bean, Cinnamon, White kidney bean, *Garcinia Cambogia,* Nopal Cactus, Hoodia, Yohimbine, *Malpighia glabra, Eurycoma Longiflolia, Carailuma Fimbriata, Citrus aurantium, Gymnema Sylvestre, Lyceum barbarum, Aloe Vera,* Cayenne, Pomegranate, Blueberry, Billberry, or extracts of such herbal ingredients, and plant sources of antioxidants. Other ingredients may be used as well in accordance with the specific embodiments disclosed hereinbelow.

Preferably, one of the additional ingredients includes caffeine or a source thereof. Suitable sources of caffeine include caffeine anhydrous, *Coffea Arabica, Coffea canephora, Camellia sinensis, Ilex paraguariensis, Guarana, Theobroma cacao,* and kola nut.

Other embodiments include specific formulations that comprise a mixture of *Alchemilla vulgaris, Olea europaea, Cuminum cyminum,* and *Mentha longiflora,* with additional ingredients to enhance weight loss, and further comprising vitamins, minerals, amino acids, and other nutrients which are commonly known in the art.

In all of the specific formulations of the invention described herein, the form specified (capsules, caplets, or tablets) were made by requesting a commercial supplier to manufacture the capsules, caplets, or tablets from the ingredients listed under each formulation using methods well known to those skilled in the art of medication and dietary supplement manufacture. That is, one skilled in such art will be able to make the capsules, caplets, and tablets described below without further explanation. In all cases, the particular excipients are chosen by the supplier to provide the desired form. Formulations according to the invention may also be in the form of a powder to be mixed with water and consumed as a beverage. One or more flavoring agents may be added to the powder as desired.

Specific Embodiments

In all of the following formulations, the weight and weight percentage of in the tables is stated per the recommend serving size for each formulation. In all cases, the Lady's Mantle (Alchemilla vulgaris), olive leaves (Olea europaea), cumin seed (Cuminum cyminum), and wild mint (Mentha longiflora) are present in the same proportions to each other as set forth the two Said articles noted above. That is, the proportions of these four ingredients in all cases are:

Alchemilla vulgaris—12 parts by weight
Olea europaea—10 parts by weight
Cuminum cyminum—5 parts by weight
Mentha longiflora—4 parts by weight Formulation No. 1

A formulation was prepared with the following ingredients:

| Ingredient | Amount (g) | % (wt.) of total |
|---|---|---|
| Lady's mantle extract (as *Alchemilla vulgaris*) - leaf | 0.303000 | 20.209323 |
| Olive extract (as *Olea europaea*) - leaf | | |
| Cumin extract (as *Cuminum cyminum*) - seed | | |
| Horsemint extract (as *Mentha longiflora*) - leaf | | |
| Vitamin C (ascorbic acid) - granular | 0.007370 | 0.491560 |
| Niacin Fine USP FCC (nicotinic acid) | 0.004061 | 0.270858 |
| Calcium D-pantothenate USP (vitamin $B_5$) | 0.002188 | 0.145934 |
| Para-amino-benzoic acid | 0.001000 | 0.066697 |
| Vegetable oil phytosterols | 0.001000 | 0.066697 |
| Vitamin $B_6$ - Pyridoxine HCl | 0.000488 | 0.032548 |
| Vitamin $B_2$ - Riboflavin USP | 0.000347 | 0.023144 |
| Vitamin $B_1$ - Thiamine HCl | 0.000306 | 0.020409 |
| Vitamin $B_{12}$ - Cyanocobalamin 1% on dicalcium phosphate | 0.000120 | 0.008004 |
| Excipients | | Remainder |

This formulation was prepared in the form of powder capsules. The recommended serving size is two capsules. It is expected that users will take three servings per day.

Formulation No. 2

A formulation was prepared with the following ingredients:

| Ingredient | Amount (g) | % (wt.) of total |
|---|---|---|
| Lady's mantle extract (as *Alchemilla vulgaris*) - leaf | 0.303000 | 16.868269 |
| Olive extract (as *Olea europaea*) - leaf | | |
| Cumin extract (as *Cuminum cyminum*) - seed | | |
| Horsemint extract (as *Mentha longiflora*) - leaf | | |
| Caffeine anhydrous USP | 0.225000 | 12.525943 |
| Ferrous gluconate dehydrate | 0.017245 | 0.960044 |
| Vitamin C (ascorbic acid) - granular | 0.007143 | 0.397657 |
| Folic acid - 10% trituration | 0.003330 | 0.185384 |
| Gamma-oryzanol | 0.001000 | 0.055671 |
| L-orthinine monohydrochloride | 0.001000 | 0.055671 |
| L-carnitine L-tartrate | 0.001000 | 0.055671 |
| Excipients | | Remainder |

This formulation was prepared in the form of liquid capsules. The recommended serving size is two capsules. It is expected that users will take three servings per day.

Formulation No. 3

A formulation was prepared with the following ingredients:

| Ingredient | Amount (g) | % (wt.) of total |
|---|---|---|
| Lady's mantle extract (as *Alchemilla vulgaris*) - leaf | 0.303000 | 17.740597 |
| Olive extract (as *Olea europaea*) - leaf | | |
| Cumin extract (as *Cuminum cyminum*) - seed | | |
| Horsemint extract (as *Mentha longiflora*) - leaf | | |
| Caffeine anhydrous USP | 0.225000 | 13.173711 |
| Sesame oil - RBDW | 0.200000 | 11.709965 |
| Calcium carbonate (heavy) | 0.150000 | 8.782474 |
| Ferrous gluconate dihydrate | 0.017245 | 1.009692 |
| Vitamin C (ascorbic acid) - granular | 0.007143 | 0.418221 |
| Folic acid - 10% trituration | 0.002000 | 0.117100 |
| L-glutamic acid HCl | 0.001000 | 0.058550 |
| L-alanine | 0.001000 | 0.058550 |
| L-isoleucine | 0.001000 | 0.058550 |
| L-serine | 0.001000 | 0.058550 |
| L-threonine | 0.001000 | 0.058550 |
| Coenzyme Q10 | 0.001000 | 0.058550 |
| L-glutathione reduced | 0.000005 | 0.000293 |
| Excipients | | Remainder |

This formulation was prepared in the form of liquid capsules. The recommended serving size is two capsules. It is expected that users will take three servings per day.

Formulation No. 4

A formulation was prepared with the following ingredients:

| Ingredient | Amount (g) | % (wt.) of total |
|---|---|---|
| Lady's mantle extract (as *Alchemilla vulgaris*) - leaf | 0.303000 | 6.046005 |
| Olive extract (as *Olea europaea*) - leaf | | |
| Cumin extract (as *Cuminum cyminum*) - seed | | |
| Horsemint extract (as *Mentha longiflora*) - leaf | | |
| Caffeine anhydrous USP | 0.180000 | 3.591686 |
| Vitamin C (ascorbic acid) - granular | 0.007143 | 0.142530 |
| Carbonyl iron | 0.006122 | 0.122157 |
| Niacin Fine USP FCC (nicotinic acid) | 0.004060 | 0.081012 |
| Calcium D-pantothenate USP (vitamin $B_5$) | 0.002188 | 0.043659 |
| Anise powder (*Pimpinella anisum*) - seed | 0.001000 | 0.019954 |
| Evening Primrose oil powder (*Oenothera biennis*) - seed | 0.001000 | 0.019954 |
| Inosine anhydrous | 0.001000 | 0.019954 |
| Ornithine alphaketoglutarate 1:1 | 0.001000 | 0.019954 |
| Papain 12,000 USP units/mg | 0.001000 | 0.019954 |
| Papaya powder (*Carica papaya*) - fruit | 0.001000 | 0.019954 |
| Sweet fig powder (*Ficus opposita*) - fruit | 0.001000 | 0.019954 |
| Folic acid - 10% trituration | 0.000800 | 0.015963 |
| Vitamin $B_6$ - Pyridoxine HCl | 0.000488 | 0.009737 |
| Vitamin $B_2$ - Riboflavin USP | 0.000347 | 0.006924 |
| Vitamin $B_1$ - Thiamine HCl | 0.000306 | 0.006106 |
| Vitamin $B_{12}$ - Cyanocobalamin 1% on dicalcium phosphate | 0.000120 | 0.002394 |
| Excipients | | Remainder |

This formulation was prepared in the form of liquid capsules. The recommended serving size is three capsules. It is expected that users will take three servings per day.

Formulation No. 5

A formulation was prepared with the following ingredients:

| Ingredient | Amount (g) | % (wt.) of total |
|---|---|---|
| Caffeine anhydrous USP | 0.200000 | 9.708738 |
| Lady's mantle extract (as *Alchemilla vulgaris*) - leaf | 0.155000 | 7.524272 |
| Olive extract (as *Olea europaea*) - leaf | | |
| Cumin extract (as *Cuminum cyminum*) - seed | | |

-continued

| Ingredient | Amount (g) | % (wt.) of total |
|---|---|---|
| Horsemint extract (as *Mentha longiflora*) - leaf | | |
| Vitamin C (ascorbic acid) - granular | 0.007000 | 0.357259 |
| Bee *propolis* powder | 0.001000 | 0.048488 |
| Boldo (as *Peurmus boldus*) - leaf | 0.001000 | 0.048488 |
| Feverfew (as *Tanacetum parthenium*) | 0.001000 | 0.048488 |
| Vitamin $B_1$ - Thiamine HCl | 0.001300 | 0.063107 |
| Vitamin $B_2$ - Riboflavin USP | 0.001600 | 0.077670 |
| Calcium D-pantothenate USP (vitamin $B_5$) | 0.007000 | 0.339806 |
| Vitamin $B_6$ - Pyridoxine HCl | 0.001800 | 0.087379 |
| Folic acid - 10% trituration | 0.000110 | 0.005340 |
| Vitamin $B_{12}$- Cyanocobalamin 1% on dicalcium phosphate | 0.000002 | 0.000090 |
| Excipients | | Remainder |

This formulation was prepared in the form of caplets. The recommended serving size is two caplets. It is expected that users will take three servings per day.

Formulation No. 6

A formulation was prepared with the following ingredients:

| Ingredient | Amount (g) | % (wt.) of total |
|---|---|---|
| Lady's mantle extract (as *Alchemilla vulgaris*) - leaf | 0.303000 | 12.142498 |
| Olive extract (as *Olea europaea*) - leaf | | |
| Cumin extract (as *Cuminum cyminum*) - seed | | |
| Horsemint extract (as *Mentha longiflora*) - leaf | | |
| Caffeine anhydrous USP | 0.180000 | 7.213365 |
| Vitamin C (ascorbic acid) - granular | 0.007368 | 0.295267 |
| Goji extract (*Lyceum barbarum*) - fruit (std.) | 0.000100 | 0.040074 |
| Acerola extract (concentrate 4-5:1) (*Malpighia glabra*) - fruit | 0.000100 | 0.040074 |
| Blueberry powder (*Vaccinium corymbosum*) - fruit | 0.000100 | 0.040074 |
| Pomegranate powder (*Punica granatum*) - fruit and seed | 0.000100 | 0.040074 |
| Bilberry extract 4:1 (*Vaccinium myrtillus*) - fruit | 0.000100 | 0.040074 |
| Excipients | | Remainder |

This formulation was prepared in the form of tablets. The recommended serving size is two tablets. It is expected that users will take three servings per day.

In tests using this formulation 13 subjects (eight females and five males) took two tablets three times daily with water before meals, for the length of time indicated in the following table (weights are in pounds), with the tabulated results:

| Subject | Gender | Start Wgt. | End Wgt. | Duration | Weight Loss |
|---|---|---|---|---|---|
| 1 | Female | 145 | 122 | 8 wks., 5 days | 23 |
| 2 | Female | 156.6 | 133.2 | 8 wks., 5 days | 23.4 |
| 3 | Male | 223.4 | 198.6 | 9 wks. | 24.8 |
| 4 | Male | 203.2 | 183.6 | 8 wks., 5 days | 19.6 |
| 5 | Female | 124.4 | 110 | 8 wks., 5 days | 14.4 |
| 6 | Female | 148.8 | 134.2 | 8 wks., 5 days | 14.6 |
| 7 | Male | 189 | 171.2 | 8 wks., 5 days | 17.8 |
| 8 | Female | 145 | 119.8 | 9 wks., 2 days | 25.2 |
| 9 | Female | 143.8 | 127.2 | 8 wks., 5 days | 16.6 |
| 10 | Male | 190.2 | 177 | 8 wks., 5 days | 13.2 |
| 11 | Male | 209.4 | 195.6 | 8 wks., 6 days | 13.8 |
| 12 | Female | 144.2 | 126.6 | 9 wks., 1 day | 17.6 |
| 13 | Female | 140.6 | 123.2 | 8 wks., 5 days | 17.4 |
| Average Overall | | 166.4 | 147.8 | | 18.6 |
| Average Female | | 143.6 | 124.5 | | 19.0 |
| Average Male | | 203.0 | 185.2 | | 17.8 |

The next table summarizes the average percentage weight loss achieved by Formulation No. 6 against results reported in Table 2 of the 2010 Said et al. paper for a comparable length of time, namely about two months (percentage weight loss=average weight loss÷average start weight).

| | Formulation No. 6 | Said 2010 |
|---|---|---|
| Overall Average | 11.2% | 6.9% |
| Female Average | 13.2% | 7.5% |
| Male Average | 8.8% | 6.0% |

The 2008 Said et al. paper reports an overall average percentage weight loss of 13.2% after three months, but the charts in Figure 5 indicate a lesser reduction in body mass index after two months than at three months. From those charts it appears that the body mass index of overweight people (Figure 5(A)) decreased from 28.5 to 26, or 8.7% (2.5÷28.5) after two months, while the body mass index of obese people (Figure 5(B)) decreased from 32.1 to 29, or 9.7% (3.1÷32.1). This study did not report separately for males and females.

Formulation No. 7

A formulation was prepared with the following ingredients:

| Ingredient | Amount (g) | % (wt.) of total |
|---|---|---|
| Sesame oil | 0.715000 | 16.798853 |
| Lady's mantle extract (as *Alchemilla vulgaris*) - leaf | 0.303000 | 7.118954 |
| Olive extract (as *Olea europaea*) - leaf | | |
| Cumin extract (as *Cuminum cyminum*) - seed | | |
| Horsemint extract (as *Mentha longiflora*) - leaf | | |
| Caffeine anhydrous USP | 0.225000 | 5.286352 |
| Vitamin C (ascorbic acid) - granular | 0.007143 | 0.167824 |
| L-Leucine powder | 0.001000 | 0.023495 |
| L-Proline | 0.001000 | 0.023495 |
| L-Methionine | 0.001000 | 0.023495 |
| L-Tyrosine | 0.001000 | 0.023495 |
| Myristic acid | 0.001000 | 0.023495 |
| Trans-ferulic acid | 0.001000 | 0.023495 |
| Cayenne pepper powder (*Capsicum frutescens*) - fruit | 0.000100 | 0.002349 |
| Excipients | | Remainder |

This formulation was prepared in the form of liquid capsules. The recommended serving size is two capsules. It is expected that users will take three servings per day.

Formulation No. 8

A formulation was prepared with the following ingredients:

| Ingredient | Amount (g) | % (wt.) of total |
|---|---|---|
| Lady's mantle extract (as *Alchemilla vulgaris*) - leaf | 0.303000 | 11.480839 |
| Olive extract (as *Olea europaea*) - leaf | | |

-continued

| Ingredient | Amount (g) | % (wt.) of total |
|---|---|---|
| Cumin extract (as *Cuminum cyminum*) - seed | | |
| Horsemint extract (as *Mentha longiflora*) - leaf | | |
| Caffeine Anhydrous USP | 0.180000 | 6.820300 |
| Vitamin C (ascorbic acid) - granular | 0.007370 | 0.279253 |
| Niacin Fine USP FCC (nicotinic acid) | 0.004061 | 0.153874 |
| Calcium D-pantothenate USP (vitamin $B_5$) | 0.002188 | 0.082905 |
| Para-amino-benzoic acid | 0.001000 | 0.037891 |
| Vegetable oil phytosterols | 0.001000 | 0.037891 |
| Vitamin $B_6$ - Pyridoxine HCl | 0.000488 | 0.018491 |
| Vitamin $B_2$- Riboflavin USP | 0.000347 | 0.013148 |
| Vitamin $B_1$- Thiamine HCl | 0.000306 | 0.011595 |
| Vitamin $B_{12}$- Cyanocobalamin 1% on dicalcium phosphate | 0.000120 | 0.004547 |
| Excipients | | Remainder |

This formulation was prepared in the form of powder capsules. The recommended serving size is two capsules. It is expected that users will take three servings per day.

Formulation No. 9

A formulation was prepared with the following ingredients:

| Ingredient | Amount (g) | % (wt.) of total |
|---|---|---|
| Liquid Conjugated linoleic acid (CLA) | 1.282051 | 70.867921 |
| Lady's mantle extract (as *Alchemilla vulgaris*) - leaf | 0.303000 | 16.748928 |
| Olive extract (as *Olea europaea*) - leaf | | |
| Cumin extract (as *Cuminum cyminum*) - seed | | |
| Horsemint extract (as *Mentha longiflora*) - leaf | | |
| Vitamin C (ascorbic acid) - granular | 0.003500 | 0.193469 |
| Excipients | | Remainder |

This formulation was prepared in the form of soft gelatin capsules. The recommended serving size is two capsules. It is expected that users will take three servings per day

SUMMARY

Those skilled in the art will readily recognize that the principles underlying the present invention has application to a wide variety of compositions comprising a mixture of *Alchemilla vulgaris, Olea europaea, Cuminum cyminum*, and *Mentha longiflora* and additional ingredients to enhance weight loss.

In that connection, only selected preferred embodiments of the invention have been depicted and described, and it will be understood that various changes and modifications can be made other than those specifically mentioned above without departing from the spirit and scope of the invention, which is defined solely by the claims that follow.

What is claimed is:

1. A method of enhancing weight loss in an overweight human individual comprising administering to the individual an effective amount of a composition consisting essentially of a mixture of *Alchemilla vulgaris, Olea europaea, Cuminum cyminum*, and *Mentha longiflora*; caffeine anhydrous; Vitamin C; *Lyceum barbarum*; *Malpighia glabra*; Blueberry; *Punica granatum*; Bilberry; and one or more excipients.

2. A method of enhancing weight loss as in claim 1, wherein the ingredients of the composition are present in the following respective forms and weight percentages:

| Ingredient | % (wt.) of total |
|---|---|
| (i) the mixture of *Alchemilla vulgaris* (leaf); *Olea europaea* (leaf); *Cuminum cyminum* (seed), and *Mentha longiflora* (leaf) | 12.142498 |
| (ii) caffeine anhydrous | 7.213365 |
| (iii) Vitamin C (ascorbic acid) - granular | 0.295267 |
| (iv) *Lyceum barbarum* - fruit | 0.040074 |
| (v) *Melpighia glabra* (concentrate 4-5:1) - fruit | 0.040074 |
| (vi) Blueberry powder (*Vaccinium corymbosum*) - fruit | 0.040074 |
| (vii) *Punica granatum* - fruit and seed | 0.040074 |
| (viii) Bilberry extract 4:1 (*Vaccinium myrtillus*) - fruit | 0.040074 |
| (ix) One or more excipients | Remainder. |

3. A method of enhancing weight loss as in claim 2, wherein the mixture ingredients are present in the mixture in the following proportions:

*Alchemilla vulgaris*—12 parts by weight;
*Olea europaea*—10 parts by weight;
*Cuminum cyminum*—5 parts by weight; and
*Mentha longiflora*—4 parts by weight.

4. A method of enhancing weight loss as in claim 3, wherein the composition is provided in tablet form, each tablet including the following amounts by weight of the respective ingredients:

| Ingredient | Weight (g) |
|---|---|
| (i) the mixture of *Alchemilla vulgaris* (leaf); *Olea europaea* (leaf); *Cuminum cyminum* (seed), and *Mentha longiflora* (leaf) | 0.303000 |
| (ii) caffeine anhydrous | 0.180000 |
| (iii) Vitamin C (ascorbic acid) - granular | 0.007368 |
| (iv) *Lyceum barbarum* - fruit | 0.000100 |
| (v) *Melpighia glabra* (concentrate 4-5:1) - fruit | 0.000100 |
| (vi) Blueberry powder (*Vaccinium corymbosum*) - fruit | 0.000100 |
| (vii) Pomegranate powder (*Punica granatum*) - fruit and seed | 0.000100 |
| (viii) Bilberry extract 4:1 (*Vaccinium myrtillus*) - fruit | 0.000100. |

5. A method of enhancing weight loss as in claim 4, wherein the method comprises administering two tablets to the individual three times a day.

* * * * *

UNITED STATES PATENT AND TRADEMARK OFFICE
CERTIFICATE OF CORRECTION

Page 1 of 1

PATENT NO. : 9,220,741 B2
APPLICATION NO. : 13/221141
DATED : December 29, 2015
INVENTOR(S) : Shawn Shirazi et al.

It is certified that error appears in the above-identified patent and that said Letters Patent is hereby corrected as shown below:

IN THE SPECIFICATION

Column 1, line 23: "(Mentha longiflora L.)" should read -- *(Mentha longiflora L.)* --.

Column 1, line 31: "*Mentha longiflora.*–20 mg" should read -- *Mentha longiflora L.*–20 mg --.

Column 2, lines 33-34 should read: -- Yohimbine, *Malpighia glabra, Eurycoma longifolia, Caralluma fimbriata, Citrus aurantium, Gymnema Sylvestre*, --.

Column 3, line 2: "(Alchemilla vulgaris)" should read -- *(Alchemilla vulgaris)* --.

Column 5, line 8: "Boldo (as *Peurmus boldus*) - leaf" should read -- Boldo (as *Peumus boldus*) - leaf --.

Column 8, line 21: "*Melpighia glabra*" should read -- *Malpighia glabra* --.

Column 8, line 45: "*Melpighia glabra*" should read -- *Malpighia glabra* --.

Signed and Sealed this
Twelfth Day of April, 2016

Michelle K. Lee
*Director of the United States Patent and Trademark Office*